United States Patent [19]

Thomas

[11] Patent Number: 4,770,878

[45] Date of Patent: Sep. 13, 1988

[54] MOLD AND DUST INHIBITING PRODUCT AND METHOD

[76] Inventor: Richard D. Thomas, 812 N. Euclid St., Fullerton, Calif. 92632

[21] Appl. No.: 27,878

[22] Filed: Mar. 19, 1987

Related U.S. Application Data

[63] Continuation-in-part of Ser. No. 606,150, May 2, 1984, which is a continuation-in-part of Ser. No. 536,262, Sep. 27, 1983, abandoned.

[51] Int. Cl.$^4$ .................... A01N 37/00; A01N 59/20
[52] U.S. Cl. ........................................ 424/141; 119/1; 424/131; 424/144; 424/147; 424/150; 424/154; 514/78; 514/557
[58] Field of Search ............... 514/557, 78; 424/131, 424/141

[56] References Cited

U.S. PATENT DOCUMENTS 3,404,987 10/1968 Kooistra et al. ............... 424/317 X
4,042,716 8/1977 Bertram et al. ............... 424/317 X
4,396,612 8/1983 Candussi et al. .................... 514/78

OTHER PUBLICATIONS

"Why Glycerine for Drugs & Cosmetics", Glycerine Producers Assn., pp. 1 & 2, 3, 1950.

*Primary Examiner*—Leonard Schenkman
*Attorney, Agent, or Firm*—Foley & Lardner, Schwartz, Jeffery, Schwaab, Mack, Blumenthal & Evans

[57] ABSTRACT

A mold and dust inhibiting composition which has particular utility in connection with the use of animal litter such as poultry litter, as well as having general utility for controlling both mold and dust. The composition of the invention is an aqueous solution of one or more salts of propionic acid, one or more deliquescent substances, and also preferably one or more humectants. Propionate ions are made available for mold control by this solution just as effectively as propionic acid, but without the disadvantages of propionic acid including a bad odor, serious corrosive characteristics, and high volatility and hence short residual time. The deliquescent, and preferably also the humectant, prevent moisture from migrating toward container walls where there is a large day/night temperature differential, and also prevent dry regions from developing and producing potentially harmful dust. Addition of lecithin to the product as a lubricant provides additional protection against dust being generated.

19 Claims, No Drawings

MOLD AND DUST INHIBITING PRODUCT AND METHOD

RELATED APPLICATIONS

The present application is a continuation-in-part of Ser. No. 606,150, filed May 2, 1984, which in turn was a continuation-in-part of Ser. No. 536,262, filed Sept. 27, 1983, and both prior applications being entitled MOLD INHIBITING PRODUCT AND METHOD OF MAKING SAME.

BACKGROUND OF THE INVENTION

1. Field of the Invention

The present invention is in the field of mold inhibitors, and also relates to the prevention of harmful dust which is likely to be generated in the handling and use of some products which also characteristically have mold problems, such as animal feeds and grains, and poultry litter.

2. Description of the Prior Art a. Mold Problems

There is a serious worldwide problem of molds growing in food materials, and particularly in animal feeds. This problem is most serious, and is a year-round problem, in tropical zones of both the eastern and western hemispheres, but it is also a problem in temperate and colder zones, particularly during the spring and fall seasons when there are frequently large temperature differentials between night and day, on the order of 30° F. or more, which can cause an accumulation of moisture in the feed adjacent the cold metal of feed tanks or bins.

One reason molds present such a serious problem is that they produce dangerous mycotoxins, some of which are carcinogenic. For example, one of the common molds, *Aspergillus flavus*, produces the mycotoxin aflatoxin which, in addition to other toxic characteristics, interferes with the immune system's ability to produce gamma globulin, the protein that is part of the immune system. The resulting breakdown of the immune system then renders animals that have ingested such mold vulnerable to a variety of diseases.

The standard product that has been used for many years for the control of molds is propionic acid $CH_3CH_2COOH$. Prior to the present invention, propionic acid has been the most reliable mold inhibitor for animal feeds, and it still remains the product of choice on a worldwide basis.

However, propionic acid has serious problems, so that it is unacceptable in many circumstances, and its use will be limited in some areas of the world, particularly in the Orient where the mold problem is severe. A major problem with propionic acid is that it has a terrible, strong odor, which is almost like the smell of urine, and when people work around propionic acid, their clothes and bodies acquire this obnoxious odor. One reason for this bad odor is that it is very volatile, so that it is rapidly released in vapor form from feeds to which it has been applied. For this reason, many people, and the people of some regions such as the Orient, will not stand for the use of propionic acid; and those who do use it are uncomfortable in such use. Also, some animals, particularly hogs, are especially sensitive to the odor of propionic acid.

Another serious problem with propionic acid is that it is highly corrosive. The only feasible place for propionic acid to be applied to feeds is in feed mill equipment, and this equipment is generally made of mild steel which is particularly vulnerable to acid corrosion. Thus, feed mill equipment in which propionic acid is added to the feeds will rapidly deteriorate from the attack of this acid.

A further serious problem with the use of propionic acid is that it has a high degree of volatility and hence short residual time.

A number of mold inhibitor products combining propionic acid with other ingredients such as acetic acid and benzoic acid have been and are currently being marketed under a variety of trademarks in an endeavor to make the products more commercially acceptable, but the principal operative ingredient of such products is still propionic acid, and such products still have the same problems of the odor and corrosiveness of propionic acid.

It has been understood in the art that it is the propionate ion $CH_3CH_2COO-$ that is the active mold inhibitor ingredient in propionic acid, so attempts have been made to use salts of propionic acid as mold inhibitors in an endeavor to overcome the odor and corrosion problems. The principal salts that have been used are the sodium and calcium salts of propionic acid, and as far as applicant is aware, these have only been used as mold inhibitors in a fine, granular form, and never in the form of a liquid solution. These propionate salts do not have an objectionable odor, and are neutral and hence not especially corrosive. The sodium propionate salt has been found satisfactory in solid form for human use in bread, this being made possible because the granular or powdered sodium propionate disperses fairly well in the wet bread dough, remaining well dispersed throughout the baked bread.

Although currently used to a limited extent in animal feeds, the dry propionate salts are not satisfactory for feeds, the principal problem being that in granular form there is insufficient contact of the propionate salt particles with the grain particles unless great quantities of the propionate salts are used. On the order of five to seven times as much of the propionate salt must be used in order to disperse it adequately through the feed to get approximately the same degree of mold inhibition as can be achieved with liquid propionic acid. This makes the use of dry propionic salts such as sodium propionate and calcium propionate economically disadvantageous as mold inhibitors for animal feeds.

Prior to the present invention, propionic acid salts have never been usable in the form of a liquid solution for treating animal feeds, even though they would be equally as effective for mold inhibiting as propionic acid because it is the propionate ion which performs the mold-inhibiting function, and the liquid would be readily dispersable in intimate contact with the feed grain particles in the same relatively small amounts as with liquid propionic acid, but without the objectionable odor and corrosive characteristics of the acid. It is believed that a reason liquid propionic salt solutions have not heretofore been used as animal feed mold inhibitors is the great propensity of the propionic salts to precipitate out of the solution in a mushy, gel-like form. Even though adequate concentrations might have been achievable under controlled laboratory or plant conditions, the long-term stability would have been unreliable for a useful mold-inhibiting product.

Another mold problem of which applicant is aware associated with the handling of animals is in poultry litter. Poultry litter is conventionally composed of wood shavings, rice hulls and the like spread out to approximately a 6-inch depth under the poultry. This mold problem is most severe around the poultry feeders where moisture tends to accumulate from droppings from the birds.

b. Dust Problems

There are also serious dust problems in connection with the use, handling, and storage of some of these same materials for which there are mold problems as described above.

One such dust problem of which applicant is aware that occurs in connection with animal feeds relates to poultry feed. The tips of poultry feed granules have a tendency to dry out and break off from the feed granules and turn into dust. Such dust when breathed in by the birds can cause serious respiratory diseases such as Aspergillosis. This same problem occurs with respect to the wood shavings, rice hulls and the like used for poultry litter. The litter tends to dry out and generate dust which, when breathed in by the birds, can cause the same diseases as feed dust.

SUMMARY OF THE INVENTION

In view of these and other problems in the art, it is a general object of the present invention to provide a liquid mold inhibitor that is as effective as propionic acid, but does not have the objectionable odor, corrosion problems, and high volatility and hence short residual time characteristic of propionic acid, and which is therefore particularly useful for controlling mold.

Another general object of the present invention is to provide a liquid mold inhibitor which, because of its effectiveness and lack of objectionable characteristics, will be acceptable in all areas of the world, and most importantly, in those tropical areas where mold is a serious problem but propionic acid will often not be used because of its bad odor and corrosive charateristics.

Another object of the invention is to provide a liquid mold inhibitor which comprises an aqueous solution of a salt of propionic acid, which may be one or more of three propionate salts, ammonium propionate, sodium propionate, and potassium propionate.

Another object of the invention is to provide a propionate salt solution mold inhibitor which includes deliquescent material, preferably one or more deliquescent substances from the group consisting of magnesium chloride, calcium chloride, manganese chloride, ferric chloride, and zinc chloride, the deliquescent material holding water in the treated product to maintain hydrolyzation and hence effectiveness of the propionate ion content of the treated product, and serving the surprising function of preventing treated materials from becoming overly damp near the walls of containers subject to large overnight temperature differentials.

Another object of the invention is to provide a liquid propionate salt solution mold inhibitor of the character described which includes one or more humectants, preferably from the group consisting of glycerol, potassium polymetaphosphate, propylene glycol, sorbitol, triacetin, mannitol, pectins, and polyhydric alcohols, the humectant trapping odor-carrying moisture molecules in the liquid solution, and also cooperating with the deliquescent material in keeping the water content of the solution up so that the propionate salt remains fully hydrolyzed and thereby fully functional as a mold inhibitor, and additionally cooperating with the deliquescent material in preventing water molecules from migrating through containers and concentrating proximate cold container walls.

A further general object of the invention is to provide a novel aqueous mold-inhibiting solution which also surprisingly and synergistically has excellent dust-inhibiting characteristics, whereby the same aqueous solution of the invention when applied to poultry litter or the like will function to either inhibit the formation and propagation of mold or inhibit the formation of dust, and under some circumstances, will perform both of these inhibiting functions with respect to a product treated by the invention.

A further, more specific object of the invention is to provide an aqueous solution containing one or more salts of propionic acid, one or more deliquescent substances, and also preferably one or more humectants, which will function both to prevent the growth of mold and prevent the production of dust with respect to treated products.

A still further object of the invention is to provide a mold and dust inhibiting aqueous solution of the character described which, while protecting poultry litter against mold, also protects poultry litter against the formation of dangerous dust which, when breathed in by birds, may cause a respiratory disease such as Aspergillosis.

Another object of the invention is to enhance the dust inhibiting function of the liquid product of the invention, by including a uniformly dispersed suspension of feed-grade lecithin in the aqueous solution of the invention, the lecithin lubricating against the production of dust by abrasion.

An additional object of the invention is to provide a mold and dust inhibiting product which functions over a long residual time.

The product of the present invention is an aqueous solution of one or more salts of propionic acid and deliquescent material, and preferably also humectant. The salt of propionic acid may be ammonium propionate, sodium propionate, or potassium propionate, or any combination of these three propionate salts. The deliquescent material may be one or more of a large number of deliquescent substances as set forth hereinafter in the Detailed Description, but is preferably one or more deliquescent substances from the group consisting of magnesium chloride, calcium chloride, manganese chloride, ferric chloride, and zinc chloride. The humectant is preferably one or more humectant substances from the group consisting of glycerol, potassium polymetaphosphate, propylene glycol, sorbitol, triacetin, mannitol, pectins, and polyhydric alcohols. The pH of the aqueous solution of the invention is preferably in the range of from approximately 6.3 to approximately 6.9, which is a substantially neutral condition of the aqueous solution. Such substantially neutral condition minimizes the volatility of the propionate ion content of the solution, and thereby helps keep odor to an absolute minimum, while at the same time the propionate ion content of the solution is fully effective for mold control, being just as effective as propionic acid. Because of this substantially neutral condition of the solution of the invention, it is generally noncorrosive, having corrosive characteristics approximating those of water.

The deliquescent material in the aqueous solution of the invention stops water from coming off of the treated product, maintaining hydrolyzation of the propionic salt and hence effectiveness of the propionate ion content for inhibiting the propagation of mold throughout the product that is treated. At the same time, it is believed that by stopping water from coming off of the treated product, the deliquescent material thereby also stops propionate ions from coming off with the water vapor, which would otherwise tend to shorten the residual time or effective operating life of the solution of the invention and also tend to cause objectionable odor. The presence of the deliquescent material in the solution of the invention also prevents dry surface areas from developing in products treated by the invention, such as poultry litter, and thereby prevents the generation of potentially harmful dust from the treated products.

The humectant which is also preferably included as a component of the aqueous solution of the invention cooperates with the deliquescent material in stopping water from coming off of the product, and hence in maintaining hydrolyzation of the propionic salt, blocking both water molecules and propionate ions from coming off of the treated materials, and in preventing the development of dry, dust-producing areas of the treated materials.

While odor control is primarily accomplished by use of propionate salt instead of propionic acid, and also by the substantially neutral condition of the solution which minimizes volatility of the propionate ion content, odor control is also aided by the water molecule-attracting power of the deliquescent material, and where humectant is included in the solution, the humectant further controls odor by inhibiting the moisture molecules from escaping the liquid solution and thereby locking odor-carrying moisture in the solution.

An additional ingredient that may be included in the solution of the invention is a substantially uniform dispersion of feed-grade lecithin.

A still further ingredient that may be included in the solution of the invention is monosodium glutamate.

DETAILED DESCRIPTION

The product of the invention is a mold and dust inhibiting aqueous solution which finds particular utility in connection with the use of animal litter such as poultry litter, as well as having general utility for controlling both mold and dust where humidity and temperature conditions are such as to make these a problem.

Mold problems are conventionally thought of as only being present in damp, humid climates. However, applicant has determined that where products are stored or transported in metal bins or containers, regardless of the humidity wide temperature variations which are likely to occur between day and night will often cause moisture migration toward and onto the walls of such bins and containers, producing a peripheral concentration of moisture which is conducive to mold propagation.

Dust problems are conventionally regarded as dry, low humidity climate problems, and those having ordinary skill in the art would not consider the possibility that a product such as the present invention which has particular utility for the control of dampness-propagated mold might also have particular utility for the control of dust. In the present invention, the novel combination of ingredients not only effectively controls the propagation of mold, but at the same time, performs what would normally be considered an opposite function of effectively controlling dust, and the present invention is desirably applied to inhibit and control mold propagation and/or dust production regardless of what environments such batches may be subjected to, and therefore without any need for selectively applying separate mold inhibiting and dust inhibiting measures according to projected environments or handlings to which the treated material may be subjected.

The principal combination of the invention is an aqueous solution of a salt of propionic acid, which is preferably ammonium propionate, sodium propionate, or potassium propionate, or any combination of these, together with a deliquescent material, which is preferably one or more deliquescent materials from the group consisting of magnesium chloride, calcium chloride, manganese chloride, ferric chloride, and zinc chloride. The invention also preferably includes one or more humectants from the preferred group consisting of glycerol, potassium polymetaphosphate, propylene glycol, sorbitol, triacetin, mannitol, pectins, and polyhydric alcohols.

Moisture control in the material to which the invention is applied is accomplished primarily by the presence of the deliquescent material, and involves stabilization of moisture in the product to which the invention is applied, both against evaporation and against movement or migration of water molecules, as described hereinafter in detail. When humectant is combined in the product of the invention, it cooperates with the deliquescent material in controlling moisture against evaporation and migration by blocking the escape of water molecules from the protected product, and is also particularly useful in controlling odor which has historically been a serious problem where propionic acid has been used for mold control.

Applicant's aqueous solution of one or more salts of propionic acid and one or more deliquescent materials, and also preferably one or more humectants, serves both of the primary inhibiting functions of the invention, namely, mold inhibiting and dust inhibiting. Nevertheless, as further assurance against the production of potentially explosion-causing dust, it is also preferred to include a fatty material, preferably feed-grade lecithin, as a substantially uniformly dispersed suspension in the aqueous solution, the lecithin or other fatty material cooperating with the other ingredients as a positive assurance against the production of dust in this situation.

An additional ingredient that may be included in the aqueous solution of the invention is monosodium glutamate (MSG).

By employing one or more salts of propionic acid instead of the state-of-the-art mold inhibitor propionic acid per se, the solution of the present invention is enabled to be made close to neutral, with a preferred pH of approximately 6.6, and a preferred pH range of from approximately 6.3 to approximately 6.9, instead of highly acidic as is propionic acid, and this in turn makes the solution much less volatile than propionic acid, which reduces the odor, and also makes the solution generally noncorrosive, having corrosive characteristics approximating those of water. A series of factors which determine this preferred pH and preferred pH range are described in detail hereinafter. The salt or salts of propionic acid embodied in the invention nevertheless have substantially the same mold-inhibiting effectiveness as propionic acid, but without its three major objectionable features, namely, disagreeable odor, highly corrosive characteristics, and high volatility and hence short residual time. Thus, the propionate salt component of the present invention gives the invention the same utilitarian capability as propionic acid, without its objectionable features, and thereby makes the invention acceptable for mold control in all areas of the world, and most importantly in those humid tropical areas where mold is a severe problem but propionic acid will not be used because of its bad odor, corrosive characteristics, and short residual time.

While all three salts of propionic acid, sodium, ammonium, and potassium, or any combination of the three, are satisfactory for the present invention, as will be appreciated from test data set forth hereinafter, ammonium propionate is presently preferred because for a selected percentage by weight of the deliquescent material or materials in the formulation, a relatively greater, and hence more effective, percentage by weight of propionate ions can be included in the formula. Next preferred is potassium propionate, because for a selected percentage by weight of deliquescent material, the next largest percentage by weight of propionate ions can be included in the formula. Least preferred of the three propionate salts is sodium propionate, because for a selected percentage by weight of deliquescent material, the least percentage by weight of propionate ions can be included in the formula of the three propionate salts.

For similar reasons, the most preferred deliquescent materials from the preferred group consisting of magnesium chloride, calcium chloride, manganese chloride, ferric chloride, and zinc chloride, are magnesium chloride, ferric chloride, manganese chloride, and zinc chloride, while the least preferred of these five deliquescent materials is calcium chloride. For a selected percentage by weight of these preferred four deliquescent materials, a larger percentage by weight of effective propionate salt is enabled to be included in the formula than can be included where calcium chloride is the selected deliquescent material. Test data supporting such selection is set forth in detail hereinafter.

Of the preferred group of humectants consisting of glycerol (glycerine), potassium polymetaphosphate, propylene glycol, sorbitol, triacetin, mannitol, pectins, and polyhydric alcohols, the presently preferred humectant is glycerol because of its widespread availability and acceptance as a food ingredient.

The presence of the deliquescent material in combination with the salt of propionic acid in applicant's aqueous solution provides a plurality of cooperative functions which, at least in part, are unexpected and surprising, and contrary to what those skilled in the art would expect. The strong attraction of the deliquescent component of the invention effectively stops water from evaporating from or coming off the poultry litter, or other treated product to which the present invention has been applied. (1) Thus, the deliquescent material prevents a reduction of moisture in the treated product which would in turn reduce hydrolyzation of the propionate salt which is necessary for maintaining the active condition of the propionic ions for performing the mold inhibiting function. (2) Also, the deliquescent material in the solution of the present invention bars evaporation of water molecules from relatively warm zones and migration of such evaporated water molecules toward relatively cold zones such as bin or container walls under climatic conditions where there is a relatively large temperature differential between day and night, preventing moist, mold-propagating zones from being generated adjacent container walls during storage and transport of such treated materials. (3) Further, it is believed that the deliquescent material, by inhibiting escape of water vapor from the treated products, stops propionate ions from coming off of the treated products with water vapor which would reduce the propionate concentration and hence the mold-inhibiting strength of the treatment, and which would also tend to cause objectionable odor. (4) Presence of the deliquescent material in the solution of the invention prevents dry, dust-producing surface zones from developing on poultry litter and the like by evaporation of moisture from such surface portions, preventing the production of dust which might be harmful when breathed in by animals such as poultry, or which might result in calamitous, explosive atmospheres in storage regions. (5) Further, the deliquescent material tends to equalize moisture or make moisture more uniform throughout the treated product by providing a relatively greater affinity for moisture in relatively drier regions of the product than in relatively wetter regions of the product, tending to reduce unwanted zones of high moisture concentration such as in litter under poultry feeders, minimizing mold-propagating moisture concentrations.

While the presently preferred deliquescent material is one or more deliquescent substances from the group consisting of magnesium chloride, calcium chloride, manganese chloride, ferric chloride, and zinc chloride, nevertheless the deliquescent material may be any one or more deliquescent chemicals from the group consisting of ammonium citrate, calcium chlorate, calcium chloride, calcium iodide, calcium nitrite, cobaltous ammonium chloride, cobaltous iodide, cupric chlorate, cupric nitrate, ferric chloride, ferric lactate, ferric nitrate, ferrous iodide, magnesium ammonium chloride, magnesium chlorate, magnesium chloride, magnesium iodide, magnesium nitrate, magnesium potassium chloride, chloride, manganese oxide, manganese sulphate, phosphoric acid, phosphorus oxide, potassium acetate, potassium carbonate, potassium iodide, potassium phosphate, sodium bisulphate, stannic sulphate, and zinc chloride.

The humectant or combination of humectants preferably included in the product of the present invention have the characteristic of opposing or blocking escape of water molecules from materials to which the present invention is applied, such as feeds, grains, or poultry litter, and by virtue of such function, the humectant or humectants cooperate with the deliquescent material in maintaining hydrolyzation of the propionic salt, avoiding the development of dry zones in the treated material, preventing evaporation of moisture from relatively warm zones so that it might be able to migrate to relatively cold zones, and in preventing propionate ions from coming off with water vapor which would tend to reduce the mold-inhibiting strength of the product and also tend to cause odor from released propionate ions.

The great reduction of odor achieved by the present invention appears to be the result of a synergistic cooperation between the substantial neutralization of propionic acid and the presence of both the deliquescent component of the solution and the humectant component of the solution. The substantially neutral propionic salt solution has a much lower volatility than propionic acid, which greatly reduces the evaporation of odor-carrying moisture to a sufficiently low level for the deliquescent material and the humectant to be able to substantially completely "lock in" the odor. A humectant has heretofore been used by applicant for control of evaporation, but applicant is not aware of any prior use of a humectant, or of a deliquescent material, coupled with neutralization for odor control, or of any such use for animal feed. In applicant's prior U.S. Pat. No. 4,008,332, issued Feb. 15, 1977 for "Microcide," a humectant and a deliquescent were used to prevent evaporation of a very thin film of microcide-containing moisture on a relatively short-term basis, unrelated to odor control.

The propionate salt solution of the present invention is produced by mixing propionic acid with base which may be ammonium hydroxide, sodium hydroxide, potassium hydroxide, or a mixture of any two or more of these three bases. The quantity of base relative to the propionic acid is adjusted to provide the desired pH. The pH of the present mold-inhibiting product solution is preferably in the range of from approximately 6.3 to approximately 6.9, which, although slightly acidic, is a substantially neutral state. The presently preferred pH for the product of the invention is approximately 6.6. There is a series of factors which form the basis for such preferred and most preferred pH ranges for the present invention. One such factor is that applicant has found that this preferred range is optimal for the effectiveness of propionic acid salt in controlling most molds. The propionic acid salt disassociates with maximum effectiveness in the aqueous solution within the pH range of approximately 6.3 to approximately 6.9, and it is the propionate ion which does the job of mold control. A second factor that applicant has found in having his preferred range of pH from about 6.3 to about 6.9 is that within this range, the solution is not substantially more corrosive than water, and this is important because the aqueous solution of the present invention is primarily applied to vegetable materials housed in mild steel containers. A third factor of importance relative to pH is that the lower the pH below approximately 6.3, the more volatile the propionate ions become, with consequent evaporation and loss of strength of applicant's solution for its intended purpose of mold inhibition, and also increased odor.

The ability of the liquid product of the invention to effectively inhibit the production of dust in connection with the use and handling of poultry litter is a surprising and synergistic functional addition to the mold-inhibiting capability of the product. The dust-inhibiting function of the product is important in several specific environmental situations of which applicant is aware. There are two separate sources where dust is commonly generated in the production of poultry. First, the tips of poultry feed particles dry and break off into dust, and this is breathed in by the birds and is a common cause of respiratory disease problems such as Aspergillosis. A separate source of dust which is a common cause of these same diseases in birds is poultry litter, which is generally in the form of wood shavings, rice hulls and the like. The litter is periodically rototilled, but nevertheless areas of the litter commonly dry out and become dusty, and when such dust is breathed in by the birds, it is likely to cause respiratory diseases such as Aspergillosis. When the poultry litter is sprayed with the liquid product of the invention, the deliquescent material in the product, and also preferably the humectant in the product, cause the moisture to be locked into the product, preventing moisture from evaporating off of surface portions of the litter. The result is that dust cannot be generated from the litter. At the same time, the liquid product of the invention protects the litter against mold where conditions are such that mold might otherwise propagate.

Applicant has discovered that a sufficient proportion of feed-grade lecithin can be uniformly dispersed in the aqueous solution of the invention to perform the surface lubricating function conventionally accomplished by adding fats. Lecithin is a waxy phospholipid or phosphatide, and applicant has found that up to one part feed-grade lecithin to four parts of applicant's liquid product can be uniformly dispersed in colloidal suspension in the aqueous solution. The lecithin has two advantages over fats. First, it does not require a separate emulsifier to be placed in a stable, uniformly dispersed suspension in the aqueous solution of the invention. Second, lecithin is a hygroscopic substance, and therefore tends to cooperate with the deliquescent material and humectant in their moisture and odor control functions.

If a fatty substance other than lecithin is embodied in the aqueous solution of the invention to assist in dust suppression, it will normally require use of a conventional emulsifying procedure in order to be placed in uniformly dispersed suspension in the solution.

The dust problem pertaining to poultry litter and the solution of such problem by use of the present invention were described above. There is also a mold problem in the use of poultry litter, which is conventionally wood shavings, rice hulls and the like, in general around feeders where liquid excrement tends to accumulate. Substantially uniform application of the liquid product of the invention to poultry litter completely solves this problem by the strong mold-inhibiting quality of the invention. The excellent odor control characteristic of the invention is important in the use of the invention with poultry litter because the large area over which the litter is spread and the fluffy, porous nature of the litter exposes a very large overall surface area to the atmosphere within the confines of the poultry housing area. Use of the conventional propionic acid mold inhibitor for this purpose would be virtually impossible because of the terrible odor which would accumulate. Despite such large exposed surface area of poultry litter, the moisture retention and odor suppression characteristics of the invention enable excellent mold-inhibiting characteristics to be maintained over an extended useful life of the litter without objectionable odor from the product of the invention.

With the product of the invention substantially uniformly dispersed throughout the litter, the invention tends to maintain a generally uniform moisture distribution throughout the litter. Where added moisture tends to accumulate around feeders, the mold-inhibiting quality of the invention has been found with repeated applications of the invention to be strong enough to prevent formation or propagation of mold in such regions.

Applicant has found that to assure long-term protection against mold and dust in most environments, 2-4 lbs. per ton of the liquid mold and dust inhibitor of the invention should be used for a moisture content of up to 14 percent by weight; and that for every 2 percent increase in moisture over 14 percent, one lb. per ton more of the product should be added. Thus, 3-5 lbs. per ton of the product should be used for a moisture content of 14-16 percent, 4-6 lbs. per ton for a moisture content of 16-18 percent, and 5-7 lbs. per ton for a moisture content of 18-20 percent. For severe mold problems, considerably more of the product of the invention may be desirable. For example, in the most severe mold problem of which applicant is aware, it may be desirable to use up to approximately 10 lbs. of the liquid product of the invention per ton.

Where feed-grade lecithin is employed in suspension with the invention, that will represent an additional weight of product per ton, preferably approximately one part by weight of lecithin to four parts by weight of the liquid product of the invention.

Limits and Proportions of the Ingredients

Upper Limits for Propionate Ions

In the following description, percentages by weight for propionate ion content in solutions of the invention are given as percentages by weight equivalent of propionic acid, of which 98.65 percent by weight is propionate ion.

In general, it is preferred that close to the maximum possible propionate ion content be provided in the product of the invention for maximum effectiveness in the function of mold inhibition, while still being a totally stable product under forseeable weather conditions (i.e., no material amount of the product being likely to precipitate out), and at the same time, enabling the presence of sufficient deliquescent material for efficient operation of the product both as a mold inhibitor and as a dust inhibitor, which includes efficient operation of the product in its water anti-migration function.

2.7 percent by weight is a desirable percentage of deliquescent material for a highly effective product according to the invention, being a sufficient amount to assure against loss of moisture and consequent dust problems in very dry climates and to assure against moisture migration where there are likely to be very wide day/night temperature variations and moisture migration would otherwise be a serious problem. With 2.7 percent by weight deliquescent material, where the salt of propionic acid is ammonium propionate, the maximum weight equivalent of propionic acid (of which 98.65 percent by weight is propionate ion) which applicant has been able to place in a stable solution of the invention is:

59% with calcium chloride as the deliquescent;
68% with magnesium chloride as the deliquescent;
68% with ferric chloride as the deliquescent;
68% with manganese chloride as the deliquescent;
68% with zinc chloride as the deliquescent.

With sodium propionate as the salt of propionic acid, for 2.7 percent by weight deliquescent material, the maximum percent by weight equivalent of propionic acid (of which 98.65 percent by weight is propionate ion) which applicant has been able to place in a stable solution of the invention is:

30% with calcium chloride as the deliquescent;
68% with magnesium chloride as the deliquescent;
68% with ferric chloride as the deliquescent;
68% with manganese chloride as the deliquescent;
68% with zinc chloride as the deliquescent.

Where the salt of propionic acid is potassium propionate, for 2.7 percent by weight of deliquescent material, the maximum percentage by weight equivalent of propionic acid (of which 98.65 percent by weight is propionate ion) which applicant has been able to place in a stable solution of the invention is:

41.7% with calcium chloride as the deliquescent;
62.4% with magnesium chloride as the deliquescent;
68% with ferric chloride as the deliquescent;
62.4% with manganese chloride as the deliquescent;
56.8% with zinc chloride as the deliquescent.

Applicant's testing indicates that where a combination of two or more of the ammonium, sodium and potassium salts of propionic acid is employed, and where a combination of two or more of the deliquescents calcium chloride, magnesium chloride, ferric chloride, manganese chloride, and zinc chloride is employed, the amounts of propionate ion and the amounts of deliquescent which may be included in a stable solution of the invention may be approximately determined by averaging from the specific test data set forth above and hereinafter for the particular ingredients.

Thus, for approximately 2.7 percent by weight of deliquescent material, for any of the three propionate salts, ammonium, sodium or potassium, or any combination thereof, and for any of the preferred five deliquescent materials or any combination thereof, applicant has found that a stable solution of the invention can always be formulated with at least approximately 30 percent by weight of propionate salt.

Also, for approximately 2.7 percent by weight of deliquescent material, applicant's test data indicates that an upper limit of approximately 68 percent by weight equivalent of propionic acid may be included in a stable solution of the invention by proper selection of the salt of propionic acid and the deliquescent material or various combinations thereof.

It is presently preferred to embody at least approximately 1.0 percent by weight of deliquescent material in the solution of the present invention to assure adequate mold inhibiting and dust inhibiting functioning of the product in various climates, including adequate water anti-migration capability. Applicant's tests indicate that approximately the following percentages by weight equivalent of propionic acid (of which 98.65 percent by weight is propionate ion) can be included in a stable product according to the invention where the amount of deliquescent material is 1.0 percent:

For ammonium propionate as the salt of propionic acid, approximately 64 percent with calcium chloride deliquescent, and approximately 73 percent with magnesium chloride, ferric chloride, manganese chloride, or zinc chloride deliquescent materials.

For sodium propionate as the salt of propionic acid, approximately 35 percent with calcium chloride deliquescent, and approximately 73 percent with magnesium chloride, ferric chloride, manganese chloride, or zinc chloride deliquescent materials.

For potassium propionate as the salt of propionic acid, approximately 46 percent with calcium chloride deliquescent, approximately 67 percent with magnesium chloride or manganese chloride deliquescent, approximately 73 percent with ferric chloride deliquescent, and approximately 62 percent with zinc chloride deliquescent.

Thus, for approximately 1.0 percent by weight of deliquescent material, for any of the three propionate salts, ammonium, sodium, or potassium, or any combination thereof, and for any of the preferred five deliquescent materials or any combination thereof, applicant's tests indicate that a stable solution of the invention can always be formulated with at least approximately 35 percent by weight of propionate salt.

Also, for approximately 1.0 percent by weight of deliquescent material, applicant's test data indicates that an upper limit of approximately 73 percent by weight equivalent of propionic acid may be included in a stable solution of the invention by proper selection of the salt of propionic acid and the deliquescent material or various combinations thereof.

To provide a guide for those skilled in the art in the selection of one or more of the five preferred deliquescent materials to be included in the solution, applicant conducted tests determining the relative proportions of each of the five preferred deliquescent materials which could be contained in a stable solution product of the invention for a selected percent by weight equivalent of propionic acid in the solution.

With ammonium propionate as the salt of propionic acid, for 55 percent by weight equivalent of propionic acid, the following percentages by weight of the five deliquescent materials which could be contained in a stable solution were:

Calcium chloride between 4.0 and 5.0 percent
Magnesium chloride between 7.0 and 8.0 percent
Ferric chloride between 8.0 and 9.0 percent
Manganese chloride between 7.0 and 8.0 percent
Zinc chloride between 9.0 and 10.0 percent.

With sodium propionate as the salt of propionic acid, and 36.7 percent by weight equivalent of propionic acid, the following percentages by weight of the five deliquescent materials which could be contained in a stable solution were:

Calcium chloride between 0.5 and 1.0 percent
Magnesium chloride between 11.0 and 12.0 percent
Ferric chloride between 0.5 and 1.0 percent
Manganese chloride between 13.0 and 14.0 percent
Zinc chloride between 1.0 and 2.0 percent.

With potassium propionate as the salt of propionic acid, and 30 percent by weight equivalent of propionic acid, the following percentages by weight of the five preferred deliquescent materials which could be included in a stable solution were:

Calcium chloride between 3.0 and 4.0 percent
Magnesium chloride between 7.0 and 8.0 percent
Ferric chloride between 7.0 and 8.0 percent
Manganese chloride between 8.0 and 9.0 percent
Zinc chloride between 8.0 and 9.0 percent.

It is apparent from the foregoing that the use of calcium chloride as the deliquescent material places a considerable limitation on the amount of propionate ion which can be contained in the solution. Nevertheless, an adequate percentage of propionate ion together with an adequate percentage of calcium chloride can be embodied in the solution of the invention for satisfactory operation of the invention in most circumstances.

Tests conducted by applicant indicate somewhat better performance of calcium chloride as a deliquescent than the other four preferred deliquescent materials, at least on a relative short-term basis, which appears to be a compensating factor making use of calcium chloride more acceptable as the deliquescent material in the present invention.

Lower Limits for Propionate Ions

Applicant is not aware of any physical basis for a specific lower limit of the percent by weight equivalent of propionic acid to be included in the solution product of the invention. Nevertheless, it is presently preferred to include at least approximately 20 percent by weight equivalent of propionic acid (of which 98.65 percent by weight is propionate ion) to assure that the product is effective as a mold and dust inhibitor under all conditions of operation. Below approximately 20 percent, the propionic salt becomes rapidly functionally and economically ineffective for performing its intended functions of inhibiting both mold and dust. It is the upper limits of propionic ion content which are important since it is preferred to include close to the maximum possible percent by weight of propionic ion content in the solution of the invention for maximum mold-inhibiting performance of the invention.

Upper Limits for the Deliquescent Material

It is preferred to not include more than approximately 10 percent deliquescent material in the solution product of the invention. Greater than 10 percent deliquescent material undesirably limits the amount of propionic ion which may be made available in the formulation, and therefore limits the basic mold-inhibiting performance which is available from the product. Nevertheless, applicant's tests indicate that up to approximately 20 percent deliquescent material may be included in the product of the invention without seriously impairing the performance of the product, although it would then be necessary to undesirably limit the percent by weight of propionate ion available in the product, particularly where the deliquescent material is calcium chloride. Any amount greater than approximately 20 percent by weight of the deliquescent material would be entirely nonutilitarian, and in very humid climates there would be an undesirable tendency for the product of the invention to take on moisture from the humid atmosphere.

Lower Limits for the Deliquescent Material

Applicant has not determined any physical basis for a specific lower limit of the percentage by weight of deliquescent material to be included in the solution product of the invention. 0.5 percent by weight of deliquescent material appears to provide satisfactory operation of the invention for most circumstances. At least approximately 1.0 percent deliquescent material is presently preferred to assure adequate operation of the invention for both mold and dust inhibiting under the various climatic conditions where the product is likely to be utilized. At least approximately 2.7 percent by weight deliquescent material is a presently most preferred amount to assure against loss of moisture and consequent dust problems under very dry climate conditions, and to assure against moisture migration where very wide day/night temperature variations might otherwise tend to cause moisture buildup adjacent container walls. A presently preferred amount of deliquescent material in the product is approximately 3.6 percent.

Humectant

The humectant is preferably any one or more humectants from the group consisting of glycerol, potassium polymetaphosphate, propylene glycol, sorbitol, triacetin, mannitol, pectins, and polyhydric alcohols. The preferred range for the amount of humectant in the product, regardless of which one or more humectants may be included, is from approximately 1.0 percent to approximately 4.0 percent by weight. Within this range, applicant has found that the humectant does not appreciably change the amounts or proportions of propionate ions and deliquescent material which may be included in a stable solution of the invention as indicated in the test results presented above.

Method for Producing the Invention

The method for producing the product of the invention is believed most clearly understandable by a description of the production of specific batch weights of the product with the ingredients in relative proportions that will produce a satisfactory embodiment of the product.

EXAMPLE 1

The total batch weight for the first example given is 300 lbs., and the product to be produced is an aqueous solution of sodium propionate in which the humectant is glycerine, and which includes MSG. In this example, the MSG will be made during the process by including hydrochloric acid and glutamic acid among the ingredients.

For this 300 lb. batch, the ingredients and amounts thereof by weight are as follows:

26.5 lbs. water
3.3 lbs. "concentrated" hydrochloric acid [HCl]
3.6 lbs. 100% glutamic acid $HOOC(CH_2)_2CH(NH_2)COOH$
7.25 lbs. 100% glycerine
3.0 lbs. deliquescent material consisting of 1.5 lbs. magnesium chloride, 1.0 lb. calcium chloride, 0.3 lb. manganese chloride, 0.1 lb. ferric chloride, and 0.1 lb. zinc chloride
110.0 lbs. 50% sodium hydroxide [NaOH]
146.35 lbs. 100% propionic acid $CH_3CH_2COOH$ The hydrochloric acid and glutamic acid are added to the water before the water is added to another of the ingredients except possibly the glycerine, and this will produce glutamic acid monohydrochloride, as follows:

ti $C_5H_9O_4N + HCl \rightarrow C_5H_{10}O_4N + Cl^-$

The glycerine is added to the water, preferably after the hydrochloric acid and glutamic acid have been added; but if desired, the glycerine may be added to the water before the hydrochloric acid and glutamic acid.

The deliquescent material is added to the water, preferably after the hydrochloric acid and glutamic acid have been added; but if desired, the deliquescent material may be added to the water before the hydrochloric acid and glutamic acid.

Then, preferably the next step is to dilute the propionic acid with the water which already contains the glutamic acid monohydrochloride and the glycerine and deliquescent material, and then the sodium hydroxide is added to the mixture. Alternatively, the sodium hydroxide may be diluted wtih the water which contains the glutamic acid monohydrochloride, and then the propionic acid added to this mixture. The first of these two alternatives is preferred, because when the water is added to the sodium hydroxide, a large amount of heat is generated, and by having the large quantity of propionic acid already present when the sodium hydroxide is added, the propionic acid will serve as a heat sink and the thermal activity will be reduced.

The chemical reaction of the propionic acid with the sodium hydroxide is as follows:

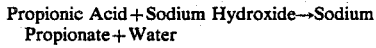
Propionic Acid + Sodium Hydroxide → Sodium Propionate + Water or

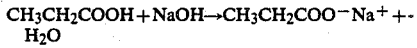
$CH_3CH_2COOH + NaOH \rightarrow CH_3CH_2COO^-Na^+ + H_2O$

In preparing a sodium propionate solution with high propionate ion concentration as is desirable for the present invention, applicant has found that when sodium hydroxide is added directly to propionic acid there is a serious precipitation problem. However, by placing all of the other ingredients, including the water, glycerine, hydrochloric acid and glutamic acid, in one of the solutions before the sodium hydroxide and propionic acid are brought together, the number of molecules per unit of space has already been diluted out sufficiently to produce a solution after completion of the acid/base reaction with all of the ingredients fully dissolved and with a high propionate ion concentration and long-term stability suitable for the purposes of the present invention.

During the reaction, the hydrochloric acid component of the glutamic acid monohydrochloride will be neutralized by the sodium hydroxide and thereby removed from the glutamic acid, and the glutamic acid will react with the sodium hydroxide to produce MSG, as follows:

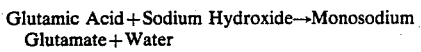
Glutamic Acid + Sodium Hydroxide → Monosodium Glutamate + Water or

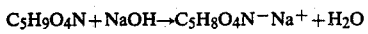
$C_5H_9O_4N + NaOH \rightarrow C_5H_8O_4N^-Na^+ + H_2O$

For this 300 lbs. batch example, there is 48.4 percent propionic acid by weight, of which 98.65 percent by weight is propionate ion. Thus, in the product of the invention that is produced in this example, there is 48.14 percent by weight of propionate ion.

If the MSG is to be added as MSG instead of being formed during the process by getting it into solution with hydrochloric acid and reacting it with sodium hydroxide, then the MSG is preferably added to the water before the water is combined with the other ingredients of the product. For the foregoing 300 lbs. batch, the 3.6 lbs. of glutamic acid used in the formulation will result in 4.14 lbs. of MSG in the final product. Accordingly, if the MSG is not made during the process but added at the end of the formulating procedure, 4.14 lbs. of MSG will be added to make the 300 lb. batch formulation in this example. In that case, without the presence of hydrochloric acid as one of the ingredients, in order to neutralize the product, 3.7 lbs. less of sodium hydroxide will be used, and then to make up the same batch weight and relative amounts of the ingredients in the batch, water will be added in the amount of 3.7 lbs. Such water is preferably added prior to the mixing together of the sodium hydroxide and propionic acid in accordance with the procedure referred to above of diluting out the number of molecules per unit of space as much as possible to work against precipitation.

In the final product, the sodium propionate ionizes in the solution to become:

$CH_3CH_2COO^-NA^+$

It is this propionate ion which is the effective mold inhibitor in the product, and it inhibits mold in the same way and with the same efficacy as the corresponding propionate ion does in propionic acid, but without the offensive odor and corrosiveness of the propionic acid.

It is to be understood that in the preparation of this first example as described above, the ingredients are to be mixed as required at the various stages.

The percentages by weight of active ingredients in this first example are approximately 48.14 percent propionate ion, 1.0 percent deliquescent material, 2.42 percent humectant, and 1.38 percent MSG, and this first example product has a pH of approximately 6.6.

EXAMPLE 2

Applicant has prepared a 100 lb. batch of the product of the invention. The ingredients for this batch were:
10.8 lbs. water
1.3 lbs. 100% MSG
2.3 lbs. 100% glycerin
1.0 lb. deliquescent material, consisting of approximately 0.5 lb. magnesium chloride, 0.33 lb. calcium chloride, 0.1 lb. magnesium chloride, 0.033 lb. ferric chloride, and 0.033 lb. zinc chloride
36.4 lbs. 50% sodium hydroxide
48.2 lbs. 100% propionic acid First, the MSG was mixed and dissolved in the water. Then the glycerine and deliquescent material were added to the water and mixed. Then the sodium hydroxide was added to the water/MSG/sodium hydroxide and mixed. Finally, the propionic acid was added to the other ingredients and mixed. The reaction was then allowed to proceed to completion, resulting in a mold-inhibiting product according to the invention having the following relative proportions by weight of the ingredients:
47.55% propionate ion
1.0 % deliquescent material
2.3 % humectant
1.3 % MSG It will be noted that some water was added in each of the above two examples. In order to provide the solution product of the present invention with maximum propionate ion content, water need not be deliberately added as in these two examples, because sufficient water for a satisfactory aqueous solution will automatically be produced in the reaction when the ingredients are mixed, from the 50 percent hydroxide component of the mixture, and also because water is a reaction product between the acid and the base. The water in the aqueous solution product enables the salt of propionic acid in the product to be substantially uniformly dispersed when the product is applied to the feed. The water also maintains the salt of propionic acid in hydrolyzed condition so that the propionate ion component of the solution is enabled to most efficiently perform its function as a mold inhibitor.

In summary, the aqueous solution product of the present invention is the first completely satisfactory mold-inhibiting product of which applicant is aware, the product having no objectionable odor or corrosion characteristics, so that the product is comfortable to use and should be acceptable on a worldwide basis. The product of the invention has been found experimentally to be fully acceptable and will not contaminate workers with any objectionable odor. In addition to its excellent mold-inhibiting characteristics, the product of the invention also has surprising and synergistic dust-inhibiting characteristics which solve heretofore very serious dust problems in connection with poultry litter.

It is to be understood that although the present invention has been described hereinabove primarily for use in connection with poultry litter mold and dust problems, the invention is fully applicable to a variety of other mold and dust problems. Accordingly, the invention is not intended to be limited to use in connection with the specific examples described herein.

While the present invention has been described herein in what are conceived to be the most practical and preferred embodiments, it is recognized that departures may be made therefrom within the scope of the invention, which is therefore not to be limited to the details disclosed herein, but is to be accorded the full scope of the appended claims.

What is claimed is:

1. A poultry litter composition comprising at least one poultry litter material and an effective dust generation inhibiting amount of a stable aqueous solution composition comprising at least one propionate salt, at least one deliquescent salt, and water.

2. A poultry litter composition according to claim 1, wherein said poultry litter material comprises at least one poultry litter material selected from the group consisting of wood particles and grain hulls.

3. A poultry litter composition according to claim 1, wherein said liquid composition has a pH in the range of from about 6.3 to about 6.9.

4. A poultry litter composition according to claim 1, wherein said propionate salt comprises at least one salt of propionic acid selected from the group consisting of ammonium propionate, sodium propionate, and potassium propionate.

5. A poultry litter composition according to claim 1, wherein sadi deliquescent salt comprises at least one deliquescent salt selected from the group consisting of ammonium citrate, calcium chlorate, calcium chloride, calcium iodide, calcium nitrite, cobaltous ammonium chloride, cobaltous iodide, cupric chlorate, cupric nitrate, ferric chloride, ferric lactate, ferric nitrate, ferrous iodide, magnesium ammonium chloride, magnesiium chlorate, magneisium chloride, magnesiium iodide, magnesium nitrate, magnesium potassium chloride, manganese chloride, manganese oxide, manganese sulphate, phosphoric acid, phosphorous oxide, potassium acetate, potassium carbonate, potassium iodide, potassium phosphate, sodium bisulphate, stannic sulphate, and zinc chloride.

6. A poultry litter composition according to claim 1, wherein said deliquescent salt comprises at least one deliquescent salt selected from the group consisting of magnesium chloride, calcium chloride, manganese chloride, ferric chloride, and zinc chloride.

7. A poultry litter composition according to claim 1, wherein said liquid composition further comprises an effective moisture stablization and propionate satbilization enhancing amount of at least one humectant.

8. A poultry litter composition according to claim 7, wherein said liquid composition has a pH in the range of from about 6.3 to about 6.9.

9. A poultry litter composition according to claim 7, wherein said humectant comprises at least one humectant selected from the group consisting of glycerol, potassium polymetaphosphate, propylene glycol, sorbitol, traicetin, mannitol, pectins, and polyhydric alcohols.

10. A method of inhibiting mold and dust generation in a poultry litter composition comprising the step of applying to said poultry litter composition an efective mold inhibiting and dust generation inhibiting amount of a stable aqueous liquid composition comprising an effective mold inhibiting amount of at least one propionate salt, an effective moisture migration inhibiting and propionate anion stbilizing amount of at least one deliquescent substance, and water.

11. A method according to claim 10, wherein said poultry litter composition comprises at least one material selected from the group consisting of wood particles and grian hulls.

12. A method according to claim 10, wherein said liquid composition has a pH in the range of from about 6.3 to about 6.9.

13. A method according to claim 10, wherein said propionate salt comprises at least one salt of propionic acid selected from the group consisting of ammonium propionate, sodium propionate, and potassium propioante.

14. A method according to claim 10, wherein said deliquescent substance comprises at least one deliquescent substance selected from the group consisting of ammonium citrate, calcium chlorate, calcium chloride, calcium iodide, calcium nitrite, cobaltous ammonium chloride, cbaltous iodide, cupric chlorate, cupric nitrate, ferric chloride, ferric lactate, ferric nitrate, ferrous iodide, magnesium ammoium chloride, magnesium chlorate, magnesium chloride, magnesium iodide, magnesium nitrate, magnesium potassium chloride, manganese chloride, manganese oxide, manganese sulphate, phosphoric acid, phosphorous oxide, potassium acetate, potassium carbonate, potassium iodide, potassium phosphate, sodium bisulphate, stannic sulphate, and zinc chloride.

15. A method according to claim 10, wherein said deliquescent substance comprises at least one deliquescent substance selected from the group consisting of magnesium chloride, calcium chloride, manganese chloride, ferric chloride, and zinc chloride.

16. A method according to claim 10, wherein said liquid composition further comprises an effective moisture stabilization and propionate stabilization enhancing amount of at least one humectant.

17. A method according to claim 16, wherein said liquid composition has a pH in the range of from about 6.3 to about 6.9.

18. A method according to claim 16, wherein said humectant comprises at least one humectant selected from the group consisting of glycerol, potassium polymetaphosphate, proylene glycol, sorbitol, triacetin, mannitol, pectins, and polyhydric alcohols.

19. A method according to claim 16, wherein said poultry litter composition comprises at least one material selected from the group consisting of wood particles and grain hulls.

* * * * *